United States Patent [19]
Yoon

[11] Patent Number: 5,613,950
[45] Date of Patent: Mar. 25, 1997

[54] MULTIFUNCTIONAL MANIPULATING INSTRUMENT FOR VARIOUS SURGICAL PROCEDURES

[76] Inventor: InBae Yoon, 2101 Highland Ridge Dr., Phoenix, Md. 21131

[21] Appl. No.: 63,486

[22] Filed: May 19, 1993

Related U.S. Application Data

[63] Continuation of Ser. No. 596,937, Oct. 15, 1990, abandoned, which is a continuation-in-part of Ser. No. 222,776, Jul. 22, 1988, abandoned.

[51] Int. Cl.⁶ .................................................. A61B 17/02
[52] U.S. Cl. .......................................... 604/105; 600/225
[58] Field of Search .................................. 604/110, 113, 604/198, 105; 128/20; 600/225

[56] References Cited

U.S. PATENT DOCUMENTS

| | | |
|---|---|---|
| 3,039,468 | 6/1962 | Price . |
| 3,253,594 | 5/1966 | Matthews et al. . |
| 3,459,175 | 8/1969 | Miller . |
| 3,495,586 | 2/1970 | Regenbogen . |
| 3,557,794 | 1/1971 | Van Patten . |
| 3,833,003 | 9/1974 | Taricco . |
| 3,952,742 | 4/1976 | Taylor . |
| 4,043,338 | 8/1977 | Homm et al. ........................ 604/105 |
| 4,077,412 | 3/1978 | Moossun . |
| 4,372,295 | 2/1983 | Hecklele . |
| 4,535,773 | 8/1985 | Yoon . |
| 4,607,619 | 8/1986 | Seike et al. . |
| 4,608,965 | 9/1986 | Anspach, Jr. et al. . |
| 4,748,982 | 6/1988 | Horzewski et al. . |
| 5,002,557 | 3/1991 | Hasson . |
| 5,041,093 | 8/1991 | Chu . |
| 5,074,871 | 12/1991 | Groshong . |
| 5,113,846 | 5/1992 | Hiltebrandt et al. .................. 604/105 |

FOREIGN PATENT DOCUMENTS 0432363  6/1991  European Pat. Off. .

*Primary Examiner*—Paul J. Hirsch

[57] ABSTRACT

Apparatus are provided for manipulating various internal tissue and organ structures of a patient incident to a variety of medical procedures. Organ or tissue manipulation is obtained through the use of one or more radially displaceable members such as balloons, expandable sponges, and various other resilient members that can be positioned about at least a portion of the periphery of a generally elongated tubular member that is insertable into the interior of the body of a patient through a portal or similar aperture formed in the body surface.

1 Claim, 10 Drawing Sheets

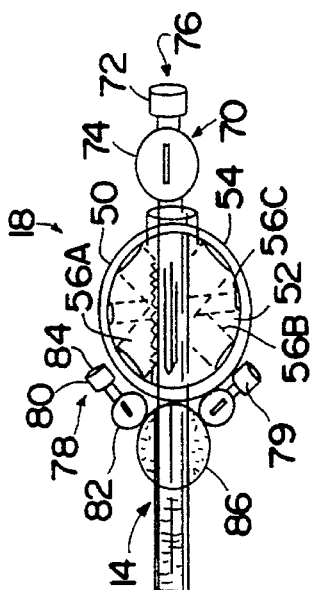
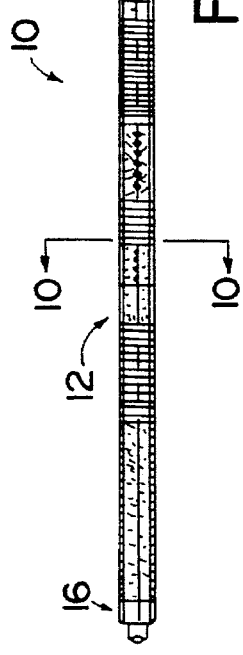
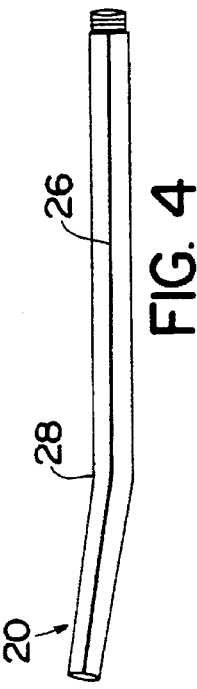
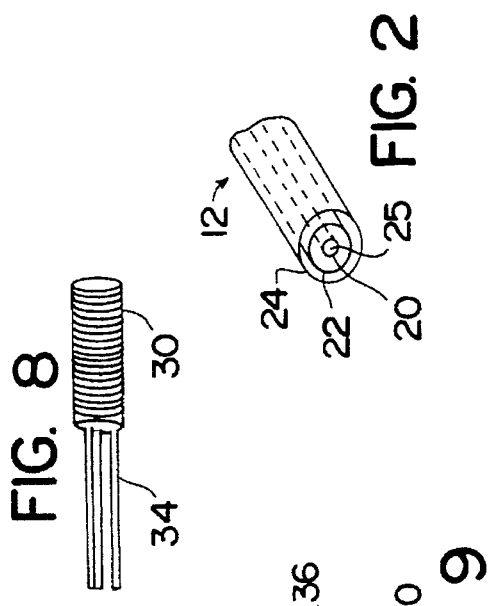

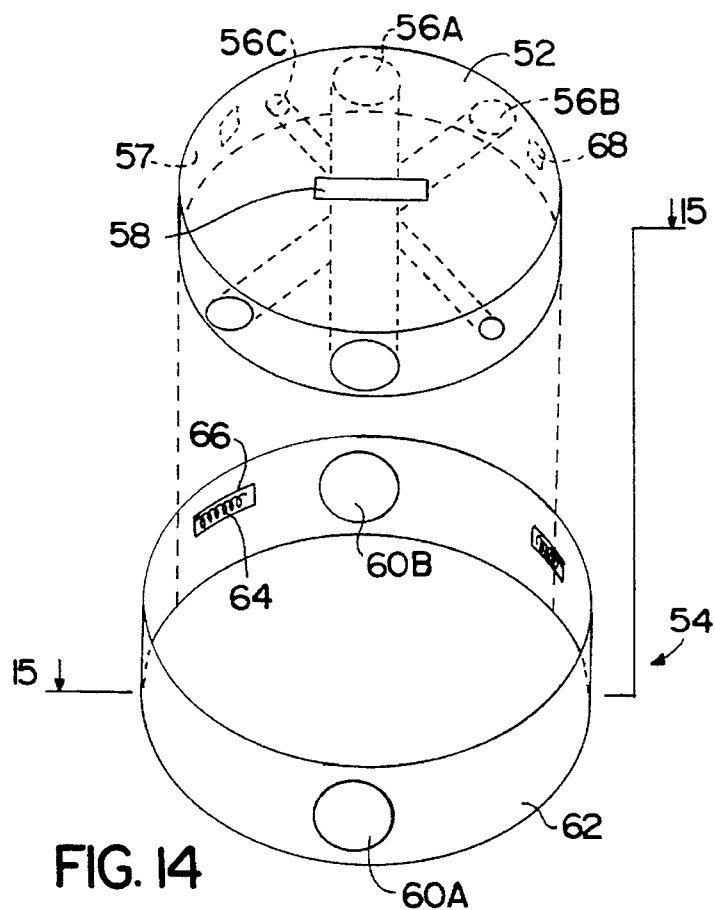
FIG. 14
FIG. 15
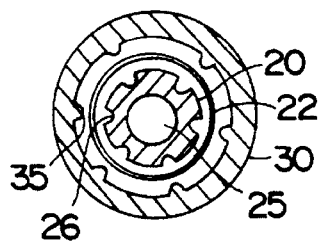
FIG. 10
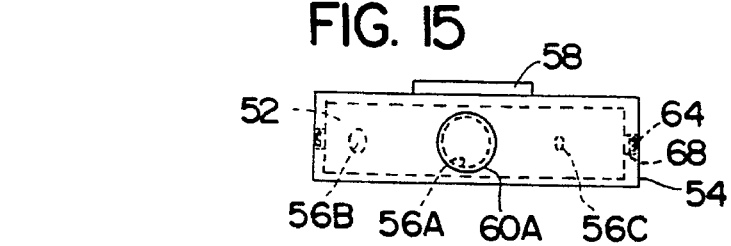
FIG. 16

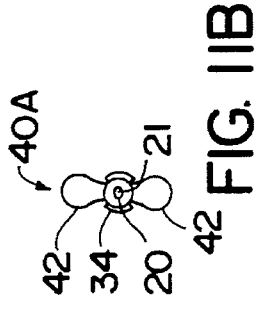
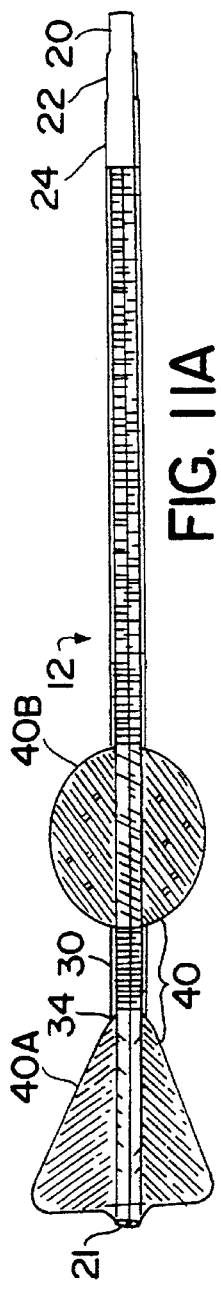
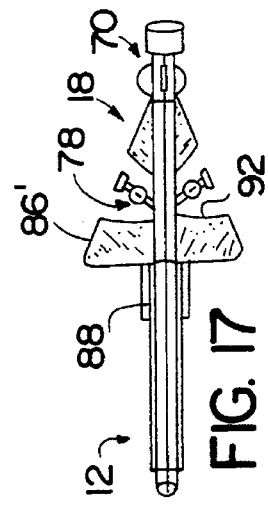
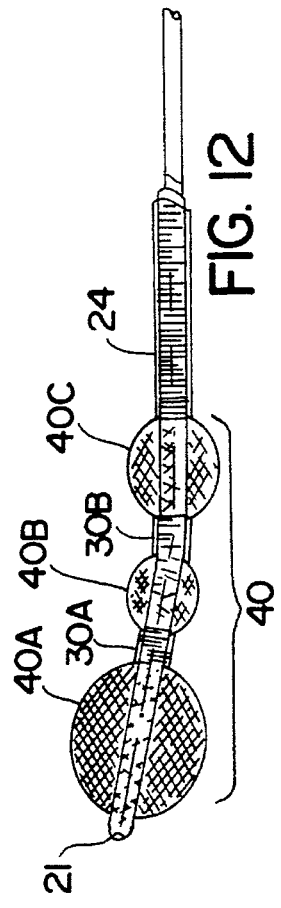
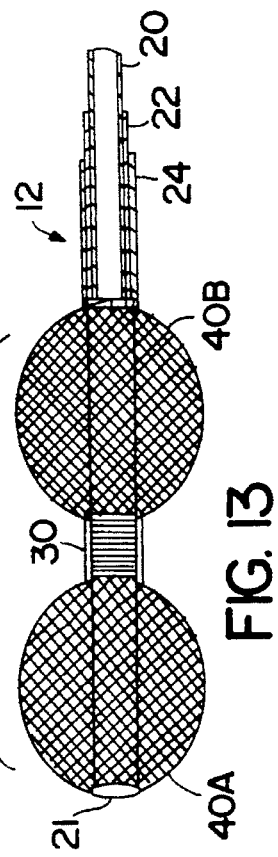

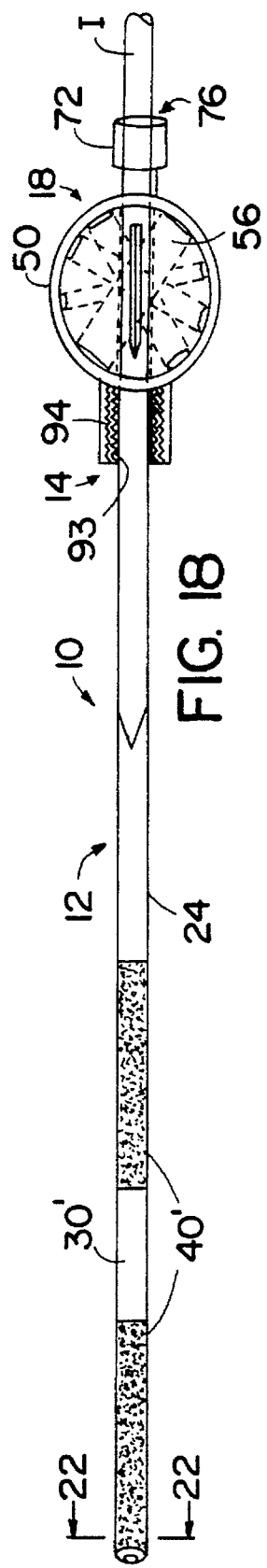
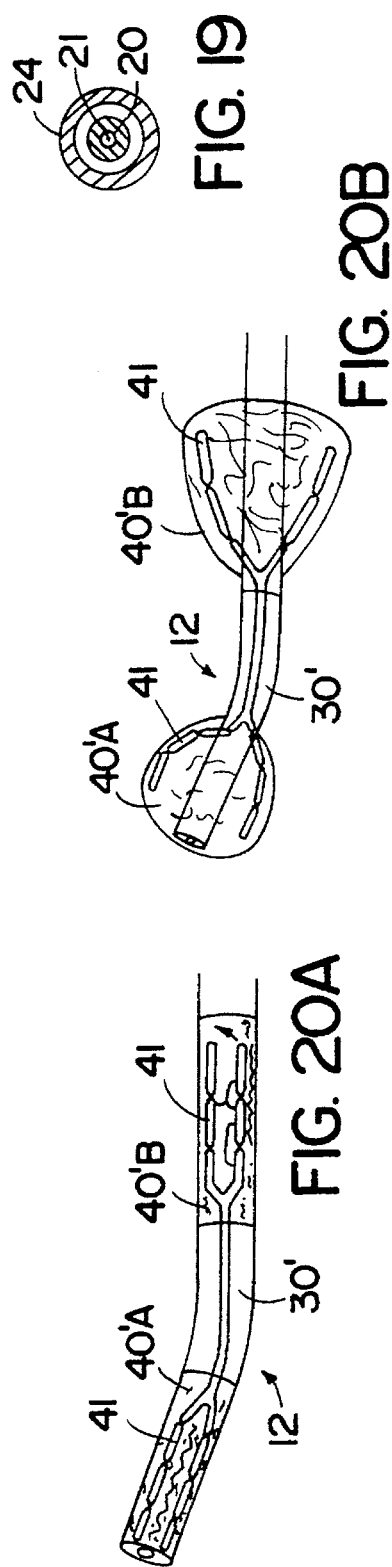
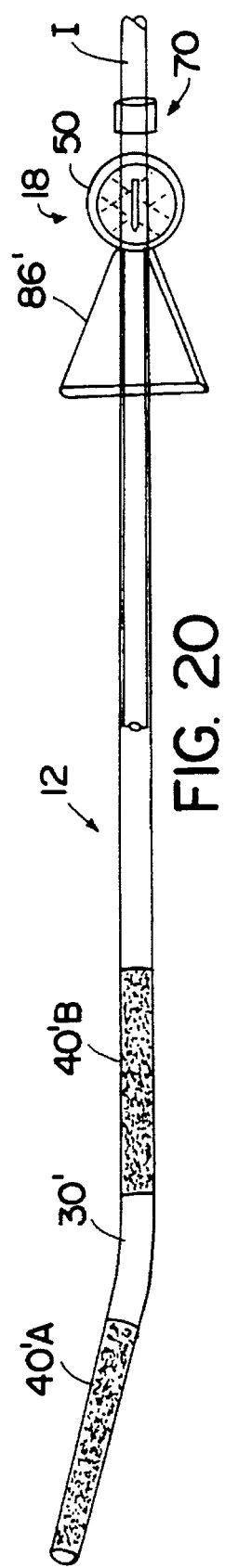

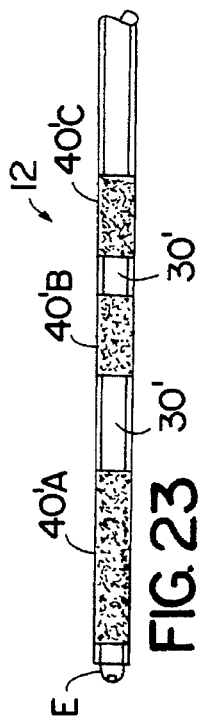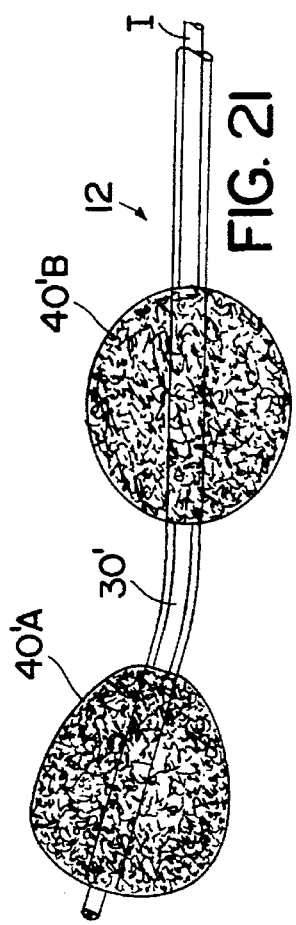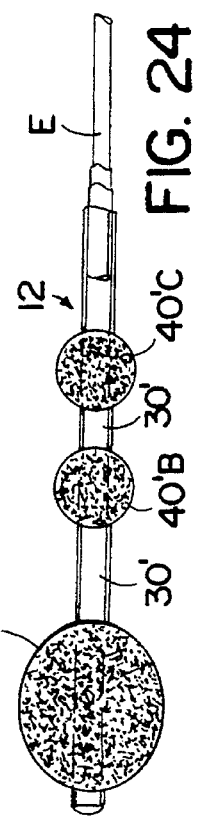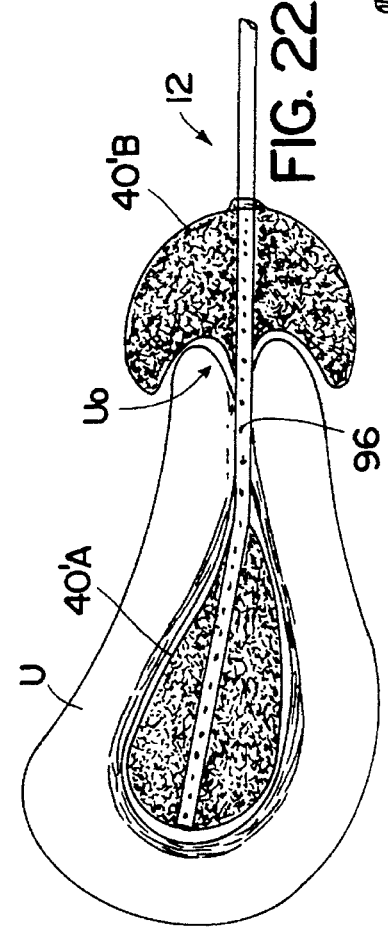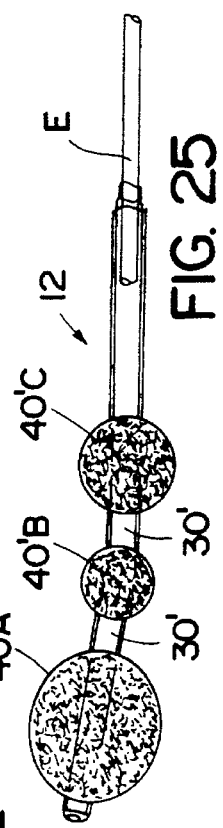

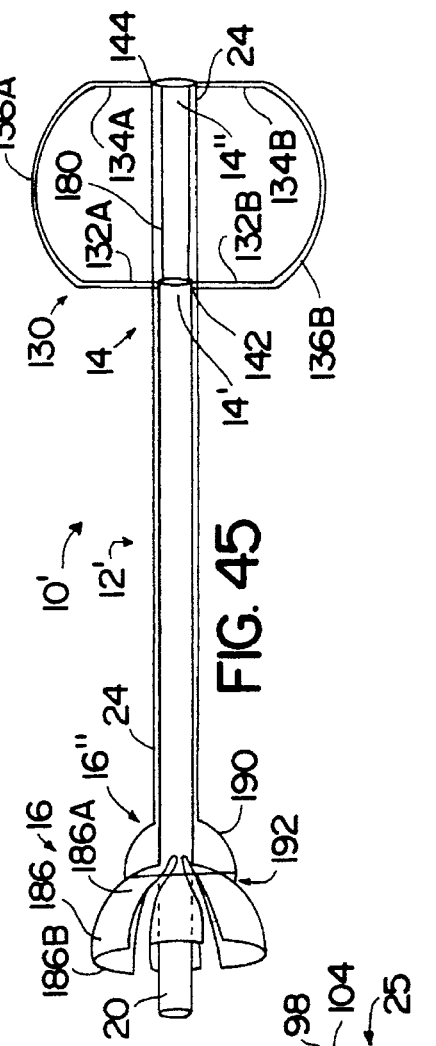

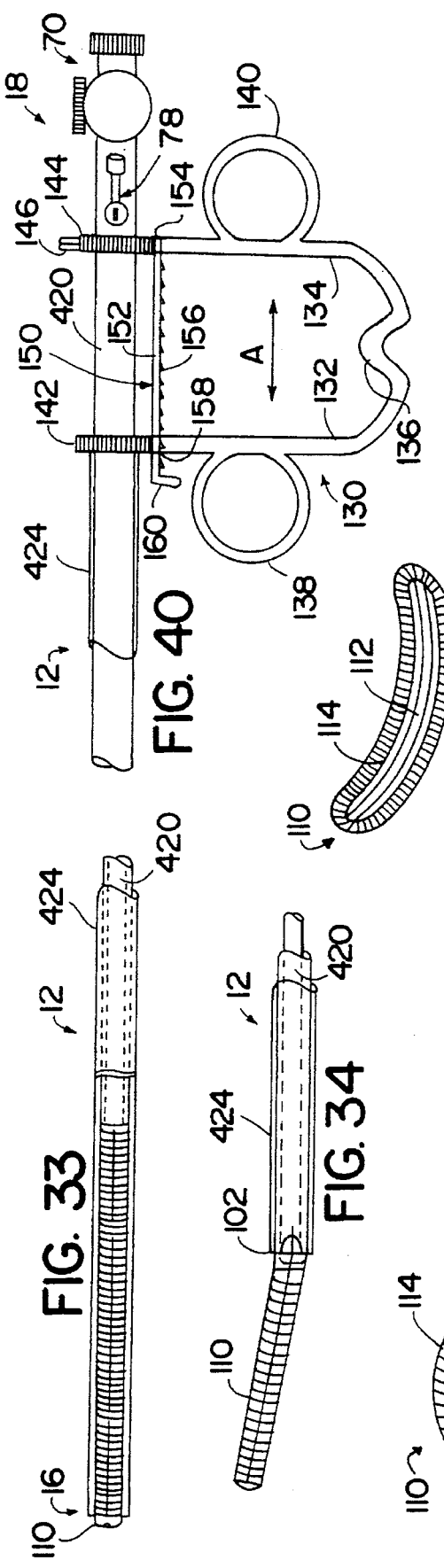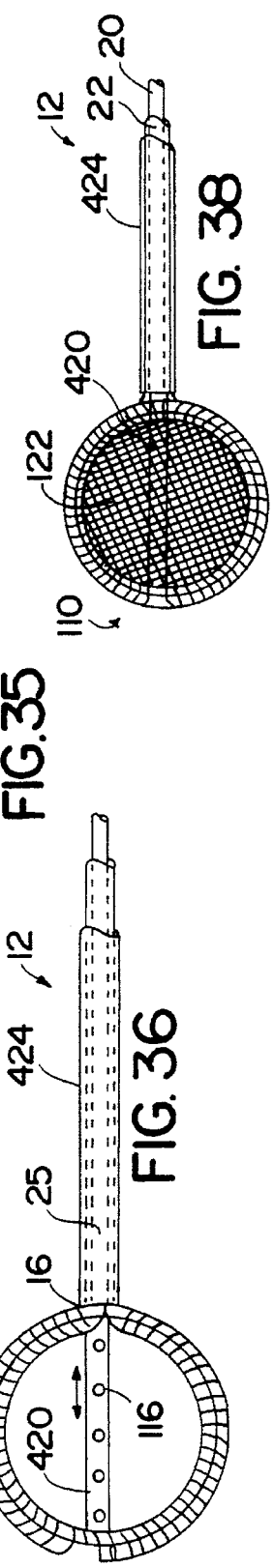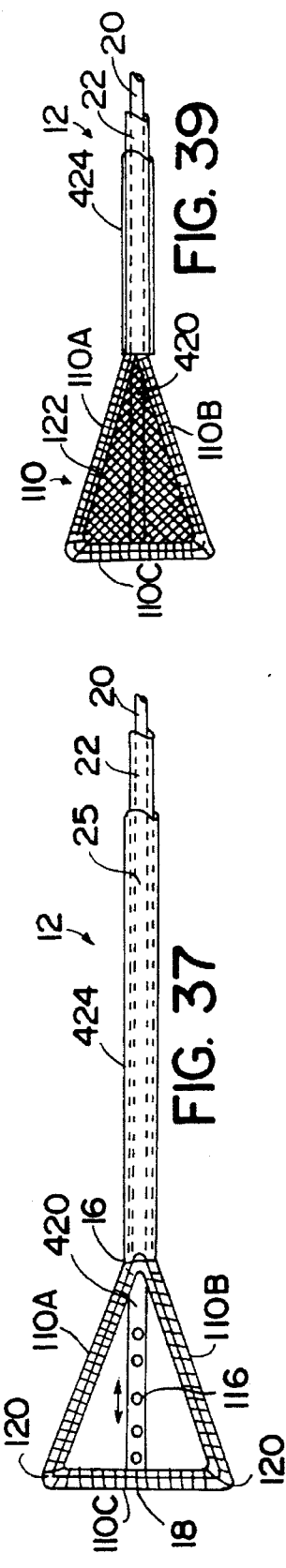

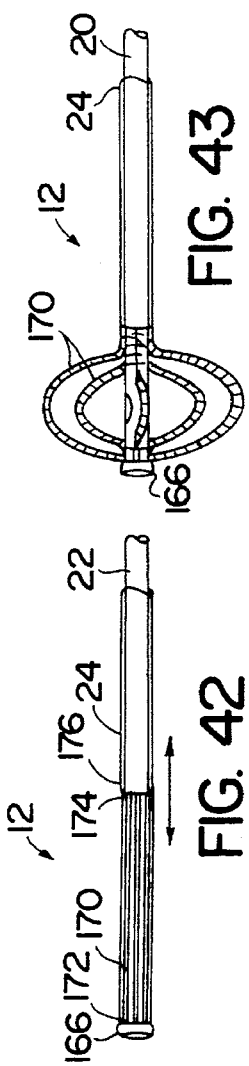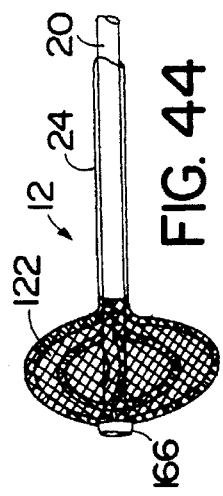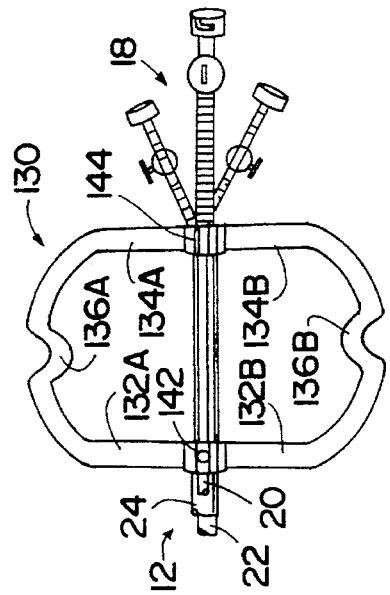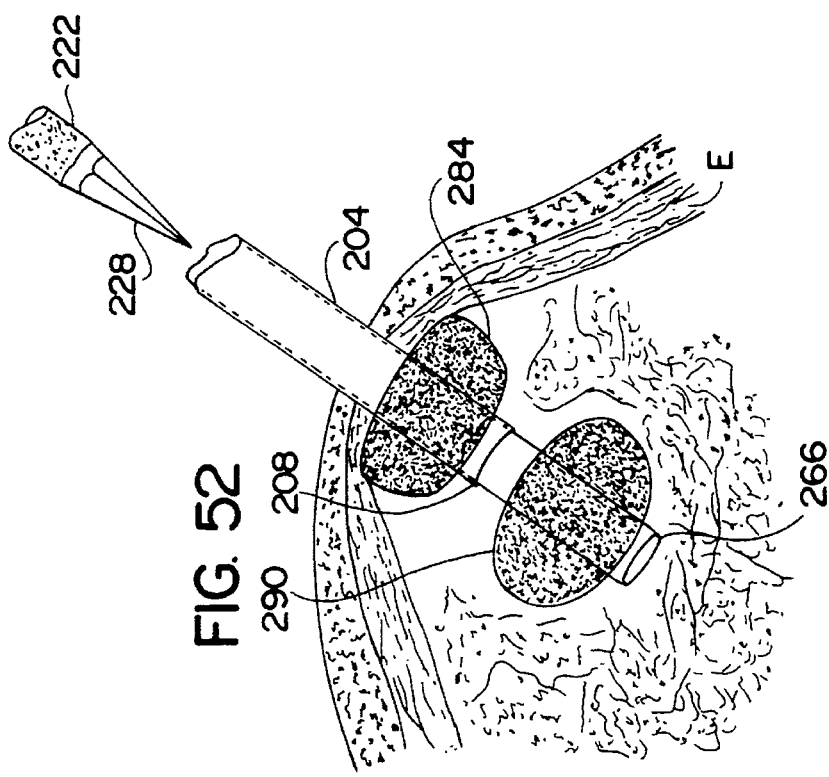

MULTIFUNCTIONAL MANIPULATING INSTRUMENT FOR VARIOUS SURGICAL PROCEDURES

CROSS-REFERENCE TO RELATED PATENT APPLICATION

This application is a continuation of application Ser. No. 07/596,937, filed Oct. 15, 1990 now abandoned, which is a continuation-in-part of my prior application, Ser. No. 222,776 filed on Jul. 22, 1988 and entitled "Multifunction Safety Trocar", now abandoned the disclosures of which are incorporated herein by reference.

BACKGROUND OF THE INVENTION

1. Field of the Invention

The invention relates generally to surgical instruments and procedures, and more particularly to surgical instruments for manipulating various tissue and organ structures such as cranial, uterine, pelvic and abdominal structures during the course of a surgical procedure. More particularly, the invention relates to surgical instruments and procedures for manipulating such organ and tissue structures from a position remote from the organ or tissue structure to be manipulated.

2. Description of the Related Art

Oftentimes during the course of a surgical procedure involving the cranial, uterine, pelvic or abdominal cavities of a patient, the need arises to manipulate various tissue and organ structures in order to better visualize the surgical field, separate adhering tissues, and displace healthy tissue from tissue to be treated incident to the surgical procedure. The need and demand for remotely controllable tissue and organ manipulating devices has increase significantly since the advent of remotely controllable fiber optic imaging systems. Surgical procedures such as exploratory knee surgery and certain gynecological procedures which only a few years ago had required relatively large incisions to be made into the respective portions of a patient's knee or abdomen now can be performed by relatively simple, remotely manipulable surgical implements which can be inserted in relatively small surgical incisions formed in the body of a patient, thereby reducing trauma to the patient and greatly diminishing patient recovery time. In view of the success that has been obtained from such surgical procedures, physicians have been anxious to expand these techniques into other types of surgical and diagnostic procedures. However, prior to the development of the subject invention, their efforts have been frustrated. For example, it would be advantageous to be able to collect tissue and/or fluid samples from remote, interior portions of the body without having to subject the patient to general anesthesia incident to conventional surgical procedures and the complications that can arise therefrom. It would further be advantageous to have a single, multifunctional manipulating instrument readily adaptable for use with a variety of different surgical implements for tissue piercing, sample collection, grasping, and manipulation.

Accordingly, it is an object of the subject invention to provide a universal, multi-purpose surgical instrument for remotely manipulating various internal structures such as cranial, uterine, pelvic and abdominal structures.

Another object of the subject invention is to provide a surgical instrument for remotely manipulating cranial, uterine, pelvic and abdominal structures during surgical procedures such as laparoscopy, hysterosalpingography, hysteroscopy, hysterectomy, endometrial tissue destruction, removal of myomas, correction of dysfunctional uterine bleeding (DUB), and other known procedures typically performed by conventional surgical techniques.

Yet a further object of the subject invention is to provide a surgical instrument for remotely manipulating cranial, uterine, pelvic and abdominal structures that permits for the use of accessory devices such as plug devices and tissue-collecting sponges.

Yet a further object of the subject invention is to provide a remotely operable surgical instrument for manipulating cranial, uterine, pelvic and abdominal structures that provides for the insertion of a variety of different surgical devices of varying size through a passage defined by the surgical instrument.

Yet still a further object of the subject invention is to provide a surgical instrument for manipulating cranial, uterine, pelvic and abdominal structures that is easy to use and manipulate, interchangeable with other devices, of uncomplicated construction, and relatively inexpensive to manufacture.

BRIEF DESCRIPTION OF THE DRAWINGS

A more complete appreciation of the subject invention and many of the attendant advantages thereof will be readily apparent by reference to the following detailed description when considered in conjunction with the accompanying drawing figures, in which:

FIG. 1 is a longitudinal sectional view of one embodiment of the invention;

FIG. 2 is a perspective view of a distal portion of the apparatus depicted in FIG. 1;

FIG. 3 is a side view of an inner tubular member of the device depicted in FIG. 1;

FIG. 4 is an alternative configuration of the inner tubular member of the apparatus depicted in FIG. 1;

FIG. 5 is a side view of a second, middle tubular member that surrounds the inner tubular members of FIGS. 3 and 4;

FIGS. 6–9 illustrate various configurations of ring-like tubular members that can comprise an outermost tubular member which surrounds the middle tubular member of FIG. 5;

FIG. 10 is a view along the line 10—10 of FIG. 1;

FIG. 11A is an enlarged longitudinal sectional view of the distal end of the apparatus depicted in FIG. 1 following balloon inflation;

FIG. 11B is an end view of the distal tip of the apparatus depicted in FIG. 11A;

FIGS. 12–13 are longitudinal sectional views of alternative aspects of the distal end of the apparatus depicted in FIG. 1 illustrating further balloon arrangements;

FIG. 14 is an exploded view of a control valve assembly of the instrument depicted in FIG. 1;

FIG. 15 is a view along the line 15—15 of FIG. 14;

FIG. 16 is a longitudinal sectional view of an alternative arrangement for the handle portion of the apparatus depicted in FIG. 1;

FIG. 17 is a longitudinal sectional view of a further alternative handle arrangement;

FIG. 18 is a longitudinal sectional view of an alternative configuration of an apparatus in accordance with the subject invention;

FIG. 19 is an end view of the distal tip of the apparatus depicted in FIG. 18;

FIG. 20 is a further alternate aspect of the apparatus of the invention;

FIGS. 20A and 20B depict alternative sponge configurations for use with the apparatus of the type depicted in FIG. 20;

FIG. 21 is a longitudinal sectional view of the distal end of the apparatus depicted in FIG. 20 following sponge expansion;

FIG. 22 is a schematic longitudinal sectional view of the apparatus of FIG. 20 positioned in the uterus of a patient;

FIG. 23 is a further alternate aspect of he distal end of the apparatus of FIG. 20;

FIGS. 24 and 25 illustrate in schematic form alternative aspects of the apparatus portion depicted in FIG. 23 following sponge expansion;

FIGS. 26 and 27 depict further alternate aspects of the distal end of the apparatus depicted in FIG. 20;

FIGS. 28–30 represent cross-sectional views of various balloon/sponge arrangements for the distalmost portion of the various apparatus of the invention;

FIGS. 31 and 32 illustrate an alternative aspect of the tubular assembly and an adjustable mounting arrangement on the instrument head assembly, respectively;

FIGS. 33–39 illustrate alternative aspects of the instrument tubular assembly;

FIG. 40 illustrates a handle arrangement for effecting relative displacement of instrument tubular members;

FIG. 41 depicts an alternative handle configuration for the surgical instrument;

FIGS. 42–44 illustrate further alternative configurations for the distal portion of the instrument tubular assembly;

FIG. 45 illustrates a further aspect of the invention having a tissue or organ grasping assembly;

FIG. 52 is a sideview of the embodiment of FIG. 51 in use in the body of a patient.

DETAILED DESCRIPTION OF THE PREFERRED EMBODIMENTS

Figure 47:
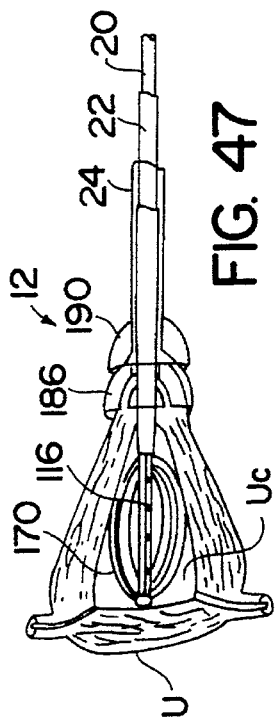
FIGS. 46–50 depict various combinations of features that can be included in the tubular assembly of the subject invention.

Referring now to the drawings, wherein like components are identified by like reference numerals throughout the various views, and in particular to FIG. 1, there is depicted by reference numeral 10 a first preferred embodiment of a surgical instrument in accordance with the present invention. The instrument 10 comprises a generally tubular body assembly 12 having proximal and distal ends 14 and 16, respectively, and a head assembly 18 mounted to the proximal end 14 of the tubular assembly 12. As used throughout this disclosure, the term "proximal" refers to the right hand portion of a referenced drawing figure, whereas the term "distal" refers to the left hand portion of the drawing figure. The tubular assembly 12 for the instrument of FIG. 1 comprises an array of three concentrically-arranged tubular members, as illustrated in FIG. 2, having a rigid or semi-rigid inner tubular member 20, a surrounding bendable, flexible or elastic middle tubular member 22, and an outermost surrounding tubular member 24. The inner tubular member 20 defines a lumen 25 through which various fluids can pass to and from the distal end thereof, as is described in detail below. With reference to FIGS. 3 and 4, the inner tubular member 20 can be configured as a straight (FIG. 3) or distally curved (FIG. 4) tubular member having one or more longitudinally-extending grooves 26 formed therein. The distally curved tubular member 20 illustrated in FIG. 4 can include one or more bends 28 for providing a predetermined or variable inclination of the tubular member so as to facilitate insertion and guidance of the instrument 10 toward the desired surgical site in the body of a patient.

The middle tubular member 22 is preferably formed from a bendable, elastic or rubber-like surgical grade material, or can alternatively be configured as a generally radially-expandable member formed from silicon or latex rubber. The tubular member 22 can alternatively be configured along a portion of its length as a radially-expandable sponge for absorbing fluids from one or more portions of the body of the patient.

The outer tube 24 of the tubular assembly 12 for the instrument of FIG. 1 can include or be in the form of one or more generally rigid or semi-rigid ring spacer members 30, as illustrated in FIGS. 6–8, for controlling the size, shape and/or location of radial expansion of the middle tubular member 22. The ring spacer members 30 can include one or more angled joints 32 to provide the member with a bent or curved configuration, as depicted in FIG. 7, for use in conjunction with angled inner tubular structures 20 of the type depicted in FIG. 4. A further aspect of the outer tubular ring spacer members 30, as depicted in FIG. 8, provides a plurality of legs 34 aligned with the longitudinal axis of the ring. The ring legs 34 define a generally rigid or semi-rigid support structure between and beyond which material from the middle tubular layer 22 can expand or be expanded for the purpose of deploying one or more balloon-like members for manipulating tissue and related structure, or for providing for the radial expansion of one or more sponge-like members, as is described in greater detail below. It will be appreciated that the tubular ring spacer members 30 can be arranged in a variety of different configurations to provide a rigid or semi-rigid support surface for forming the radially-extendable middle layer 22 in a desired configuration. For example, the ring spacer members 30 can be provided with a pair of opposed, non-parallel end walls 36, as shown in FIG. 9, for shaping the portion of the middle tube 22 upon radial expansion thereof so that the expanded middle tubular portion extends partially back over the overlying ring spacer members 30.

Means for securing in place the ring spacer members 30 along user-selected portions of the tubular assembly 12 is illustrated in FIG. 10. The inner surface of each ring spacer members 30 is depicted as including a plurality of inwardly-protruding ridges 35 that are radially arranged so as to be receivable within correspondingly-dimensioned grooves or slots 26 formed along the outer surface of the inner tubular member 20. The ridges 35 preferably extend substantially the entire length of each of the spacer members, whereas the slots are preferably configured so as to extend continuously from the proximal end of the tubular assembly 12 to their respective ends. The ring spacer members 30 can be provided with a closed, generally annular cross-sectional configuration as shown, in which case the spacer members can be slidably advanced over an end of the tubular assembly toward a desired location. Alternatively, the spacer members can be configured as generally C-shaped or U-shaped members in cross-section that are adapted to resiliently deform and engage the tubular assembly upon application over a user-selected section of the assembly 12. While an arrangement of six mutually engageable ridges 35 and slots 35 is depicted for effecting mutual interlocking engagement between the ring spacer members 30 and the inner tubular member 20, interlocking engagement can be effected by an altogether different number and spatial arrangement of ridges and slots.

FIG. 11A illustrates one preferred arrangement for radial expansion of the middle tubular layer 22 of the instrument 10 depicted in FIG. 1. In this aspect of the tubular assembly 12, the middle tubular structure 22 has been radially-expanded to form a pair of semi-deformable, tissue-manipulating balloons 40. The most distally arranged balloon, designated by reference character 40a, is arranged as a generally triangularly configured, bilaterally-expanded structure that is comprised of a pair of generally opposed lobes 42 (FIG. 11B) formed by expansion of the middle tube 22 between rigid outer ring legs 34 of the adjoining outer tubular ring spacer member 30. The proximally positioned balloon, designated by reference character 40b, is provided with a generally circular cross-sectional configuration by virtue of the opposed, generally non-parallel end walls 36 of the ring spacer member 30 (FIG. 9) between which the balloon material is expanded. It can readily be appreciated by persons of ordinary skill in the art that balloons having a variety of prescribed cross-sectional and longitudinal configurations can be obtained by forming the middle tube 20 from an appropriate combination of expandable materials and by appropriately dimensioning and configuring the outer ring spacer members 30 of the outer tubular layer 24.

FIG. 12 illustrates a further alternative balloon arrangement for the distal end of the tubular assembly 12. As is shown in the drawing, an arrangement of three balloons, designated 40a, 40b and 40c, can be provided that are spaced apart from one another by tubular ring spacer members 30 of appropriate length to arrive at the desired spatial relationship for the balloons. For example, the most distal balloon 40a can be provided with an appropriate shape such as the depicted generally circular configuration for hysteroscopic use. The intermediary balloon 40b can be spaced from the distal balloon 40a an appropriate distance by a selected rigid outer ring spacer member, designated 30a in the drawing, so that the intermediary balloon 40b, once deployed, closes off the internal cervical os of the uterus of a patient following insertion of the tubular assembly 12 therein. The most proximally-positioned balloon 40c can be spaced from the intermediary balloon 40b by a rigid ring spacer member, designated 30b, so as to close off the external cervical os of the patient. It will be appreciated that the configuration and dimensions of ring spacer members 30a and 30b separating balloons 40a and 40b, and 40b and 40c, respectively, can vary in accordance with the spatial relationship between tissues and organs in an anatomical site to be evaluated. Furthermore, the balloon size can be varied in accordance with the function to be served by the balloon and the anatomical site in which the balloon is to be positioned. For example, a balloon used to substantially close off an internal cavity, such as balloon 40c for closing off the external cervical os of a patient, can be provided with a different size and cross-sectional configuration from the balloon 40a for manipulating the uterus. Furthermore, the relative spacing of the balloons 40a, 40b and 40c can be varied as the site of a deployment and characteristics of the patient require through the use of appropriate ring spacer members 30 depicted in FIGS. 6–9. For example, in the distal tubular assembly configuration depicted in FIG. 13, two balloons 40a and 40b of substantially similar size and configuration are provided. The balloons are separated from one another by a single rigid ring spacer member 30 of the type depicted in FIGS. 6–9 having a predetermined length that is sufficient to provide the desired degree of spatial separation of the balloons 40a and 40b that is desired for a particular task. Such a configuration as depicted can be desirable for separating tissues or organ structures that are undesirably adhered to one another, or for elevating structures such as the abdominal wall from underlying tissue and organ structure so as to improve visibility and access to a surgical site thereunder.

Referring once again to FIG. 1, the head assembly 18 will now be described in greater detail. The head assembly comprises a valve assembly, designated in general by reference numeral 50, for selectively opening and closing the proximal end of the lumen 25 of the inner tubular structure 20. The valve assembly 50 is comprised of a valve head 52 that is rotatably or otherwise displaceably received within a valve body 54, and is preferably configured as an adjustable valve assembly having a variety of different sized conduits, designated 56a, 56b and 56c, formed in the valve head 52 for communication with the tubular lumen 25. The provision of a valve assembly having a variety of different sized conduits formed therein is desirable, for it permits for the use of a variety of instruments of various diameters that can be inserted through the valve assembly and into the innermost tubular lumen 25.

Further details of the valve assembly 50 are depicted in FIGS. 14 and 15. As shown in the drawings, the valve head 52 defines a plurality of conduits 56a, 56b and 56c of different diameters that extend through the sidewall 57 of the valve head. While three conduits of different size are shown, it is to be understood that a greater or lesser number of conduits of a variety of cross-sectional configurations can be provided. A handling knob 58 is provided at an upper end of the valve head to facilitate adjustment of the valve head 52 so that the desired conduit can be aligned with the front and rear apertures 60a and 60b formed in the sidewall 62 of the valve body 54. Preferably, biasing means such as spring biasing members 64 are provided so as to orient the valve head 52 within the valve body 54 in a predetermined manner. However, any other appropriate biasing means, can be provided by an arrangement of resilient bands and the like, can be substituted for the spring members 64 discussed above. The biasing members 64 are mounted within slots 66 formed in the sidewall 62 of the valve body and are arranged to cooperate with outwardly-extending shoulders 68 formed on the valve head sidewall 57. The biasing members 64 and shoulders 68 are cooperably arranged such that rotational displacement of the valve head relative to the valve body in either direction is resisted such that, upon release of the handling knob 58, the valve head assumes a position of conduit non-alignment with the valve body apertures. Predisposed non-alignment of the valve head conduits and valve body apertures is desirable, for many internal and sub-cutaneous surgical and diagnostic procedures utilize a fluid such as air or carbon dioxide gas to obtain or enhance tissue or organ structure separation so as to facilitate visualization, access and/or treatment of remote internal anatomical structures. Accordingly, predisposed non-alignment of the valve conduits and apertures minimizes the escape of such fluids through the instrument tubular lumen 25 and valve assembly 50. However, the valve head can be mounted within the valve body so as to be predisposed toward alignment of one of the conduits thereof with the valve body apertures, if desired.

An instrument inlet assembly 70 (FIG. 1) is positioned proximally of the valve assembly 50. The inlet assembly comprises a conduit 72 and a stopcock valve 74 that can be of conventional design for closing off an internal passageway 76 defined by the inlet conduit. The passageway 76 is axially aligned with the valve body apertures 60a and 60b and is provided with a substantially uniform diameter throughout its length. Alternatively, the passageway 76 can be configured with a gradually increasing diameter toward its proximal end to provide an outward taper to facilitate insertion of a surgical instrument therethrough. The respective diameters of the valve assembly passageways 56a, 56b and 56c are preferably arranged to be nominally larger than the respective diameters of the various surgical instruments to be inserted therethrough so as to provide lateral support for the inserted instrument and to minimize the occurrence and size of gaps between the instrument and the passageway walls through which fluid such as air or carbon dioxide present at the surgical site could inadvertently pass.

One or more supplemental conduits 78 can be provided to permit access to the lumen 25 for the insertion of additional instruments, supplies or fluids for communication with the anatomical site under study. The supplemental conduits can be positioned distally of the valve assembly 50 in the manner depicted in FIG. 1, or they can be incorporated into the valve assembly 50 or positioned proximally thereof, if desired. Each of the supplemental conduits 78 is comprised of a conduit inlet 80 and a stopcock valve 82 for selectively opening and closing a passageway 84 defined by the inlet. A handle 86 positioned adjacent the supplemental inlet conduits 78 can be provided to facilitate grasping and manipulation of the instrument 10 and to inhibit further insertion of the surgical instrument into the body of a patient beyond a predetermined position of the instrument. The handle 86 can be provided with a variety of configurations in accordance with the user's preference and the procedure for which the instrument 10 is to be used, and can be formed integrally with the tubular and head assemblies 12 and 18 as shown in FIG. 1, or can be detachably mounted to either or both of the respective tubular and head assemblies.

FIG. 16 illustrates an alternate configuration for the head assembly 18 of the instrument 10. In the illustrated arrangement, inlet assembly 70 extends through the handle 86 and communicates directly with the lumen 25 of the tubular assembly inner tube 20. Supplemental conduits 78 positioned on either side of the inlet assembly 70 are provided to permit for the access of additional apparatus and fluids to the central lumen 25 in the manner described above. Alternatively, the supplemental inlets 78 can be arranged such that fluid to be delivered to the surgical site trough the lumen 25 enters through a predetermined conduit, such as the conduit designated by reference character 78a, and exits from the surgical site through a separate supplemental conduit, designated by reference character 78b in the drawing. The supplemental conduits 78a and 78b are preferably arranged as generally flexible tubular members so as to provide a degree of manipulability by the user. The tubular members are preferably formed from a suitable resilient material such as double or triple layered coil spring tubes that provide for substantially leak-proof communication between the supplemental conduits 78 and the tubular assembly 12. Flexible mounting of the supplemental conduits 78 also prolongs longevity of the instrument 10 as a whole, as these types of conduits have heretofore been rigidly mounted to the various surgical instruments of the prior art and have been susceptible to breakage therefrom when the instrument is inadvertently mishandled or dropped. These supplemental conduits 78, because of their generally diminutive size, are not readily replaceable. As a result, breakage of one or more of the supplemental conduits can render the entire instrument inoperative.

The handle 86 can further be provided with a collar 88 which extends distally therefrom and which defines a recess 90 that is dimensioned to received the proximal end 14 of the tubular assembly 12. The collar recess 90 can be formed so as to exhibit a constant or diminishing diameter inwardly from its free end so as to securably retain the proximal end of the tubular assembly 12 upon insertion therein. The proximal end of the tubular assembly can be coupled to the instrument inlet assembly 70 and supplemental conduits 78 in a conventional manner, as by frictional engagement upon insertion of the tubular member proximal end over the inlet conduit 72, or by threaded engagement of the tubular assembly with corresponding threads formed along the interior of the collar 88. The distal end 92 of the supplemental conduits 78 can be configured so as to puncture the middle tubular layer 22 to provide a fluid communication path with the array of longitudinal slots 26. Fluid such as air directed through one or more of the supplemental conduits and along the slots 26 provides for inflation of the arrangement of one or more balloons 40, as discussed above. It will be appreciated that the provision of detachable mounting of the tubular assembly 12 with respect to the head assembly 18 in the manner described above permits for interchangeable mounting of tubular assemblies 12 in accordance with the procedure to be performed and the physical attributes of the patient. Detachable mounting of the tubular assembly 12 also permits for fabrication of the assembly 12 from suitable materials which render it disposable following use with a patient or for collecting tissue or fluid specimens from a patient in the manner described below. The head assembly 18 can likewise be configured as a disposable unit, thereby minimizing the possibility of the transfer of contaminants from one patient to another incident to treatment with the surgical instruments 10 as described herein.

FIG. 17 illustrates a further aspect of the head assembly 18 of the subject invention in which the handle 86' is provided with a configuration which is indicative of the organ structure in which the surgical instrument is to be employed. In the drawing, the handle 86' is provided with a generally triangular configuration which generally resembles the longitudinal sectional configuration of the human uterus. Configuring the handle 86' in this manner can be quite helpful, for the provision of such a visual indicator can assist the user in keeping him informed as to the general orientation of the organ or tissue structure into which the instrument is inserted during he course of a medical procedure. As shown, the handle is provided with a pair of generally opposed recessed cavities 92 within which are mounted the supplemental inlet conduits 78. Mounting of the inlet conduits 78 in this manner so that they are recessed with respect to the exterior surface of the handle 86' helps to protect the conduits 78 from breakage that could otherwise occur as a result of instrument mishandling.

With reference to FIGS. 18 and 19, there is depicted a further aspect of the surgical instrument of the subject invention. The tubular assembly 12 is comprised of an array of two concentrically-arranged tubular members 20 and 24, a head assembly 18 having a multipassage valve assembly 50 of the type described above, and an inlet assembly 70 which defines a passageway 76 that communicates with any one of the passageways 56 provided in the valve assembly 50. Any one of a plurality of surgical instruments I, such as an endoscope or trocar, can be inserted through the passageway 76 and correspondingly-dimensioned valve assembly passageway 56 so as to extend into the lumen 25 defined by the inner tubular member 20. The distal portion of the tubular assembly 12 can be formed from a rigid, semi-rigid, bendable or flexible tube and can be configured with a generally straight configuration, as shown in FIG. 18 or with a curved or angled configuration, as shown in FIG. 20. The instrument depicted in FIG. 20 further illustrates use of the anatomically configured handle 86' described above for assisting the user in maintaining a sense of instrument orientation within the body of a patient. In the respective drawing figures, the distal portion of the tubular assembly 12 is provided with a pair of sponges 40' which are radially expandable upon absorption of various bodily fluids. The sponges 40' are separated from one another by a tubular collar 30' having any one of a variety of predetermined lengths and shapes suitable for providing a desired spatial separation between the two sponges 40'. Alternatively, the distal end of the tubular assembly 12 can be provided with a suitable absorbant, sponge-like material along all or a portion of its length and outer surface and can be separated into two or more sections upon securement thereover of one or more tubular collar members 30'. The proximal end 14 of the tubular assembly 12 can be formed integrally with the head assembly 18, or can be disengageably connectable therewith in the manner described above or by way of mutual engagement of a threaded tube portion 93 with threaded collar recess 94, as shown in FIG. 18.

FIG. 21 illustrates the configuration of the sponges 40' of the tubular assembly 12 of FIG. 20 following the absorption of fluid. The sponges 40' can be provided with a variety of different shapes and cross-sectional configurations in accordance with the anatomical site in which they are to be used. For example, the distalmost sponge, designated 40'a can be provided with a generally conical expanded configuration for use in correspondingly-shaped structures such as the uterus of a patient. The proximally-mounted sponge, designated 40'b, can be provided with a rounded, generally circular or oval configuration for obstructing one of the cervical os adjacent the uterus.

With reference to FIGS. 20A and 20B, an appropriately configured sponge support structure, designated generally by reference numeral 41, can be provided to facilitate sponge expansion to a desired configuration upon the exposure to and absorption of fluid. The support structure is preferably configured as a collapsible structure such that it is in a generally flat configuration that is generally aligned with the longitudinal axis of the tubular assembly 12 prior to the time the sponge is exposed to fluid, as shown in FIG. 20A. Upon exposure of the sponge to fluid, such as that found in the peritoneal or other body cavities, the sponge is guided by the support structure 41 toward the desired expanded sponge configuration, as shown in FIG. 20B.

An endoscope or other surgical instrument I can be extended through the lumen 25 of the inner tubular assembly tube 20, even when the sponges 40' have been expanded, as shown in the drawing. The radially expanded sponges 40' can be deformed by surrounding tissue and organ structures, as illustrated in FIG. 22. FIG. 22 illustrates deployment of the surgical instrument 10 in the uterus of a patient. In the instrument embodiment depicted in FIG. 22, the distal end of the tubular assembly is provided with a plurality of apertures 96 that extend from the outer surface of the tubular assembly to the lumen 25. The sponge material is mounted both above and below the apertures 96 so as to expand in a bi-lobed manner analogous to that depicted in FIGS. 11A and 11B upon absorption of fluid. Fluid can be ejected from lumen 25 through the apertures thereof in accordance with a prescribed medical treatment. Distal sponge 40'a as shown has expanded upon absorption of fluid within the uterus and has been moderately deformed by surrounding tissues to assume a somewhat elongated, conical configuration. Proximal sponge 40'b is separated from the distal sponge 40'a by collar 30' and is positioned adjacent the external cervical os $U_o$. As shown in the drawing, the sponge 40'b has been deformed as a result of insertion of the instrument 10 so as to close off and surround the external cervical os $U_o$.

FIGS. 23–25 illustrate further sponge configurations for the distal portion of the tubular assembly 12. For example, in FIG. 23 there is depicted an array of three expandable sponges 40'a, 40'b and 40'c separated from one another by collar members 30' of prescribed length and shape. The length of the tubular collars 30 can be selected so as to provide the degree of desired spatial separation of the sponges for the reasons noted above. FIG. 24 illustrates the configuration of the sponges of FIG. 23 following the absorption of fluid. FIG. 25 illustrates angular inclination of the distal most portion of the tubular assembly 12 in a manner consistent with the apparatus depicted in FIG. 20. It is, of course, to be appreciated that the tubular assembly 12 can be comprised of a myriad of combinations of balloons 40, sponges 40', or any combination thereof in accordance with the desired objectives of the medical procedure.

FIGS. 26 and 27 illustrate a further aspect of the tubular assembly 12 of the instrument of the subject invention. As illustrated in FIG. 26, the inner tube 320 can be arranged so as to be telescopically received within the outer tubular member 324 so as to provide a user selectable and variable separation distance between the distalmost balloon 40a or sponge 40'a and the proximal balloon 40b or sponge 40'b of the tubular assembly. As noted previously, balloons 40 and sponges 40' can be included with the same tubular assembly, as illustrated in the respective FIGS. 26 and 27. FIG. 27 illustrates the configuration of the apparatus of FIG. 26 following expansion of balloon 40a and fluid absorption by the sponge 40'b. The respective balloons and sponges can be provided with a variety of sizes and configurations in accordance with the medical procedure to be performed. For example, circumferential, bi-lobed and tri-lobed balloon or sponge configurations can be provided along any portion of the tubular assembly in accordance with the provision of ring spacer members 30, 30' as illustrated respectively in FIGS. 28–30. A surgical instrument I such as an endoscope, probe, trocar or other surgical implement can be inserted through the lumen 25 defined by the inner tube 20.

In a further aspect of the invention, as shown in FIGS. 31 and 32, the tubular assembly 12 is provided with retaining means 98 such as a conventional thumb wheel locking device for mounting to a locking bar 100 of the head assembly 18. The tubular assembly 12 is provided with a selectively inflatable balloon 40 that can be inflated by air or a similar fluid that is delivered thereto through a channel 102 formed in the tubular member 24'. The channel 102 is in fluid communication with an external supply of fluid through an aperture 104 formed in the locking means 98. However, other suitable arrangements for selectively inflating and deflating the balloon 40 can be provided The tubular assembly 12 of FIG. 31 is mounted to the head assembly 18 by aligning the locking device 98 thereof with one of the plurality of slots 105 formed on the locking bar 100, as shown in FIG. 32. The position of the tubular assembly 12 relative to the locking bar can be adjusted so as to accommodate the internal configuration of the patient so as to obtain optimal positioning of one or more balloons 40 or sponges 40' within the patient. The central lumen 25 of the assembly 12 is configured to receive any of a variety of surgical instruments I, as shown in the drawing.

FIGS. 33–37 illustrate further configurations for the tubular assembly 12 of the subject invention. With respect to FIG. 33, the tubular assembly 12 comprises an outer tubular member 424 which telescopically receives an inner tubular member 420. Positioned at the distal end of the inner tubular member 420 is a resilient spring member 110 which can be axially aligned with the inner tubular member 420, as shown in FIG. 33, or mounted for angular extension therefrom, as shown in FIG. 34, following extension beyond the distal end 16 of the instrument. The spring member 110 can be formed from any suitable material such as rubber, plastic or metal, and can be arranged in a variety of different configurations in accordance with the desired objective of the surgical procedure. For example, the spring member 110 can be in the form of a gently curved structure defining an open cavity 112 between walls 114 of the spring. Such curvalinear tubular spring members are useful for resiliently manipulating organ tissue such as that found in the uterus. When the spring members 110 are formed from electrically conductive material, they can be used for conducting an electric current so as to effect tissue oblation or coagulation of abnormal tissue lesions.

FIGS. 36 and 37 illustrate further arrangements for the extendable resilient spring member of FIG. 33. In the arrangement depicted in FIG. 36, the spring member 110 is arranged so as to have a generally circular configuration upon full extension of the inner tube 420 outwardly from the distal end 16 of the instrument. A plurality of apertures 116 can be provided in the inner tubular member to provide for the administering of various fluids from the lumen 25 of the inner tubular member. The proximal end of the spring member 110 can be secured by conventional means to the distal end 16 of the instrument so that, as the tube 420 is displaced distally in the manner described below, the spring member 110 is extended from its housed position within the outer tube 424 to assume the generally annular configuration depicted in the drawing. In an alternate arrangement, as depicted in FIG. 37, the spring member is configured as a generally triangular member that is comprised of a pair of lateral legs 110a, 110b which extend laterally outwardly from their respective points of connection with the distal end 16 of the instrument to meet with a base leg 110c. The base leg 110c is pivotably mounted at its midsection 118 to the distal end of tubular member 420, and the lateral legs 110a and 110b are pivotably mounted to the base leg 110c by flexible joints 120 to permit relative movement of the respective legs and base leg incident to displacement of the tubular member 420 in the direction of the arrow. A plurality of apertures 116 can be provided in the distal portion of the tubular member 420 to provide for the dispensing of various fluids therethrough, as discussed above.

FIGS. 38 and 39 illustrate further variations of the arrangement depicted in FIGS. 36 and 37, respectively, in which the spring members 110 are surrounded by a resilient membrane 122. The membrane 122 can be formed from a variety of materials such as expandable rubber, fluid or cell-absorbable material such as paper or sponge, or an electrically conductive metallic material arranged as a mesh-like screen for the delivery of electric current to surrounding organ or tissue structures incident to electrocoagulation or ablation, as discussed above.

FIG. 40 illustrates a handle arrangement for effecting relative displacement of the tubular members of the tubular assembly incident to operation of the various aspects of the invention depicted in FIGS. 33–38. The handle 130 is comprised of a distal arm 132 and a proximal arm 134 connected to one another by a spring member 136. The arms 132, 134 and spring member can be arranged as discrete members pivotably mounted to one another, or they can be formed as an integral, unitary member, as shown. Manipulating rings 138, 140 can be mounted to the arms 132, 134, respectively, to facilitate relative displacement of the handle arms by an instrument user in the manner described below. As shown in the drawing, the free end of distal arm 132 is connected at shoulder 142 to outer tubular member 424 of the tubular assembly 12, whereas the free end of the proximal handle arm 134 is connected at shoulder 144 to the inner tubular member 424. The inner tubular member can be arranged so as to be provided, or in fluid communication with, an instrument inlet assembly 70 and one or more supplemental inlet conduit assemblies 78 of the type described in detail above. The handle 130 can be arranged so as to be permanently connected at shoulders 142 and 144 to the respective tubular members 424, 420 and instrument inlet assembly 70, or can be arranged so as to be disengageably connected thereto, as by forming the exterior of the respective tubular members 424, 420 and inlet assembly with threads so as to be received by complementary threads formed in the inner surface of the respective shoulders 142 and 144. Configuring the instrument as a disassembleable device facilitates instrument cleaning and sterilization, as well as providing for the fabrication of various instrument components as tubular assemblies 12 and head assemblies from suitable, single use disposable materials.

Relative displacement of the handle arms 132 and 134 in the direction of the arrow A in the drawing effects relative movement of tubular members 420 and 424 so as to extend and retract the resilient members 110 depicted in FIGS. 33–39 and discussed above. The relative position of the handle arms 132 and 134 can be fixed by locking means 150 extending between the handle arms. The depicted locking means includes a locking arm 152 pivotably connected by pivot pin 154 to proximal arm 134 that is provided with a plurality of retaining members 156 along at least a portion of the exterior surface of the locking arm. The retaining members cooperate with complementary retaining means formed in a slot or aperture 158 formed in the opposite handle arm 132. A handle 160 can be provided at the free end of the locking arm 152 to facilitate manipulation of the arm 152 relative to the slot 158. The retaining members 156 can be provided with a variety of configurations, such as grooves, slots, and apertures, or can be configured as outwardly and angularly extending projections, as shown. The retaining means of the slot 158 is correspondingly configured as may be appropriate to engage and retain the retaining members 156 thereagainst upon manipulation of the locking arm 152 relative to the slot 158 so as to fix the relative position of the handle arms 132, 134 and the tubular members 424, 420 connected thereto. It will be appreciated that the coupling arrangement of the handle arms 132, 134 and the tubular members 424, 420 can be reversed from that described above such that distal arm 132 is connected to inner tubular member 420 and proximal arm 134 is connected to outer tubular member 424 so as to maximize flexibility in the tubular assembly coupling arrangements.

FIG. 41 illustrates an alternative handle arrangement to that depicted in FIG. 40, in which the handle 130 is configured as a bilateral member comprised of opposed upper and lower distal arms 132a and 132b and upper and lower proximal arms 134a and 134b, in which upper and lower handle arm pairs 132a, 134a and 132b and 134b are joined to one another, respectively, by corresponding upper and lower handle spring members 136a and 136b. The opposed distal arms 132a and 132b are connected to one another at shoulder 142, whereas the opposed proximal arms 134a and 134b are connected at shoulder 144. The tubular and head assemblies 12 and 18 can be disengageably or permanently coupled to the respective shoulders 142 and 144, as discussed above. Likewise, the coupling arrangement between the shoulders 142, 144 and tubular members can be varied in the manner described above to permit coupling of the shoulders 142, 144 with desired ones of the tubular members 420 and 424 so as to permit relative displacement of the tubular members in a desired manner.

FIGS. 42–44 illustrate further alternative configurations for the distal portion of the tubular assembly 12. With respect to FIG. 42, the inner and outer tubular members 420 and 424 are arranged for relative displacement along their respective longitudinal axes in the direction of the arrow in accordance with the manner in which they are connected to the shoulders 142 and 144 of the handle 130. For example, the outer tube 424 can be arranged so as to extend toward the distal tip 166 of the fixedly positioned inner tubular member 420, or the inner tubular member 420 can be arranged so as to be telescopically received within outer tubular member 424, as depicted in the drawing. The portion of the inner tube 420 extending outwardly from the outer tube 424 is provided with a plurality of resilient strips 170 arranged about the periphery of the inner tubular member and generally parallel to its longitudinal axis. The distal end 172 of each resilient strip 170 is connected to the distal tip 166 of the tubular member 420, whereas the proximal end 174 is connected to the distal end 176 of the outer tubular member. Upon retraction of the inner tube 420 toward the outer tubular member 424 (or extension of outer tubular member 424 toward tip 166), each of the resilient strips flexes and assumes an outwardly bowed configuration, as shown in FIG. 43. The strips 170 can be formed from a variety of different materials, such as rubber, flexible plastic, or wire and can be covered with a flexible membrane covering 122, as shown in FIG. 44, for all of the reasons noted above in connection with the discussion of FIGS. 38 and 39.

With reference to FIG. 45, there is depicted a further aspect of the surgical instrument of the subject invention that is particularly beneficial for medical procedures such as hysteroscopy and operative hysteroscopy where it is desirable or necessary to grasp organ or tissue structures. The instrument 10' is provided with a tubular assembly 12' that can be either permanently or detachably mounted at the proximal end 14 thereof to an instrument handle 130. The tubular assembly includes an arrangement of concentrically arranged inner and outer tubular members 420 and 424, respectively, that are mounted to the handle 130 for relative displacement thereby. In the depicted arrangement, distal handle arms 132a and 132b are coupled by shoulder 142 to the proximal end 14' of the inner tubular member 420, whereas proximal handle arms 134a and 134b are coupled by shoulder 144 to the proximal end 14" of the outer tubular member 424. Spring members 136a and 136b connect corresponding upper and lower handle arm pairs 132a, 134a and 132b, 134b, respectively. A pair of opposed, longitudinally-disposed slots 180 are formed in the outer tubular member 424 to permit coupling of the handle arms 132a and 132b to their respective portions of the inner tubular member 420 and to permit proximal directional displacement of the inner tubular member 420.

Extending generally radially outwardly from the distal end 16 of the tubular assembly, and more particularly from the distal end 16' of the inner tubular member 420, are a plurality of curved flange members 186. The flange members are arranged in generally opposed pairs and are mounted to the tubular member 420 so as to be predisposed toward attaining an open orientation, as shown in the drawing. Positioned at the distal end 16" of the outer tubular member 424 is means 190 for urging the flanges 186 toward one another so as to attain a closed orientation with the flanges abutting or nearly abutting one another. The flange closing means 190 can be arranged in a variety of configurations, such as the cup-shaped member having its open end open toward the flanges 186 so as to engage a back end 186a of each flange upon operation of the handle 130 in the manner described above so as to retract the inner tubular member 420 into the outer tubular member 424 or extend the outer tubular member 424 distally, thereby urging the free ends 186b of the flanges against the proximally diminishing cross-section of the cup-shaped member.

Figure 46:
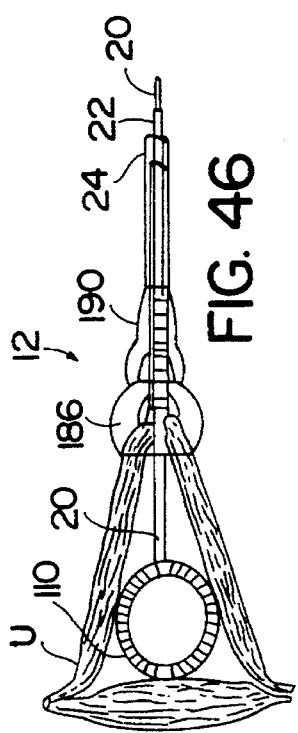

Various combinations of features of the tubular assemblies 12 described above and depicted in the various drawing figures can be obtained from the foregoing description, as depicted in FIGS. 46–50. For example, FIG. 46 depicts deployment of a tubular assembly 12 in the uterus U of a patient having the combination of a resilient member 110 positioned at the distal end of the inner tubular member 420 and a plurality of flanges 186 and flange closing means 190, as discussed above. In this depicted arrangement, the flanges are mounted to middle concentric tubular member 422 (FIG. 2) and the flange closing means 190 is mounted to the outer tubular member 424. However, it is to be appreciated that other mounting arrangements with respect to the concentric array of tubular members 420, 422 and 424 is possible.

FIG. 47 illustrates a further variation of the tubular assembly 12 in which the assembly 12 is provided with the combination of an arrangement of plurality of resilient strips 170 that are mounted to the distal end of the inner tubular member 420 in the manner described above and a plurality of flanges 186 and flange closing means 190 that are operable in the manner described above in connection with FIGS. 49 and 50. Fluid can be introduced through the lateral apertures 116 formed in the inner tubular member incident to the medical procedure being conducted. As shown in FIGS. 46 and 47, the flanges 186 and flange closing means 190 have been positioned so as to grasp the portion of the uterus adjacent the external cervical os to substantially close off the uterine cavity $U_c$. Grasping of tissue or organ structure in this manner can be advantageous in instances where it is desirable to maintain cavity closure during the course of moderate to intensive organ or tissue manipulation. Such a degree of cavity closure cannot always be attained from an arrangement of balloons and sponges. Such manipulation can occur in certain gynecological procedures, where medicinal or contrast media is introduced through apertures 116 into the uterine cavity $U_c$ prior to or during the course of protracted organ manipulation. Medicinal or imaging benefits can be considerably diminished if the fluid introduced into the organ cavity $U_c$ is permitted to flow therefrom through the cavity inlet prior to completion of the medical procedure.

Figure 48:
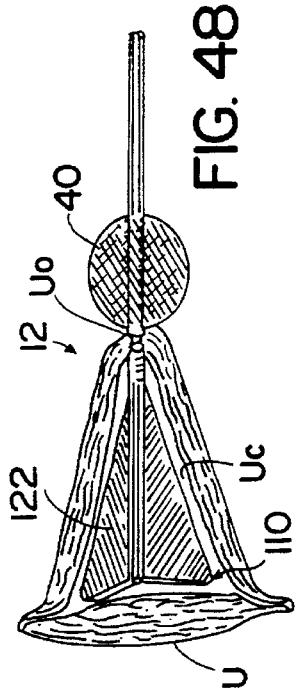

FIG. 48 illustrates a further alternative tubular assembly arrangement in which the assembly 12 is provided at its distal end with the generally triangular-shaped resilient, member 110 discussed above in connection with FIGS. 41 and 43 that is surrounded by a membrane 122 of resilient absorbable material. A balloon 40 is spaced proximally from the resilient member 110 an appropriate distance such that the external cervical os $U_o$ of the uterus U can be closed off following insertion and deployment of the resilient member in the uterine cavity $U_c$.

Figure 50:
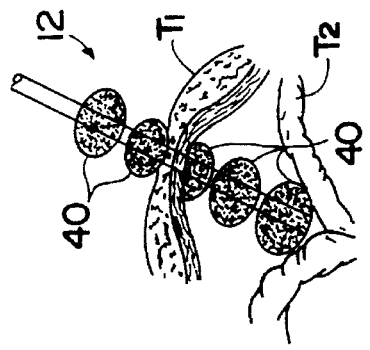
Figure 49:
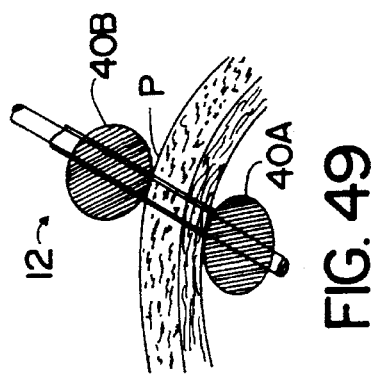

FIGS. 49 and 50 illustrate further configurational arrangements for the tubular assembly, in which a plurality of balloon members 40 are provided to close off an aperture or perforation P formed in a tissue or organ structure (FIG. 49) or to elevate one tissue or organ structure relative to another (FIG. 50). With respect to the arrangement depicted in FIG. 49, the balloons 40 are inflated only after the tubular assembly 12 has been positioned such that the distal balloon 40*a* is positioned on one side of the aperture P and the proximal balloon 40*b* is positioned on the other side of the aperture. Once the assembly 12 has been positioned in this manner, the balloons 40*a*, 40*b* can be inflated in the manner described above to close off the aperture. With respect to the arrangement in FIG. 50, the balloons 40 are inflated once the tubular assembly 12 has been appropriately positioned with respect to the two tissue or organ sections $T_1$, $T_2$ so that the tissue segments can be gently separated from one another incident to various exploratory procedures where the presence of bodily fluid may have caused undesirable adhering of tissue.

Figure 51:
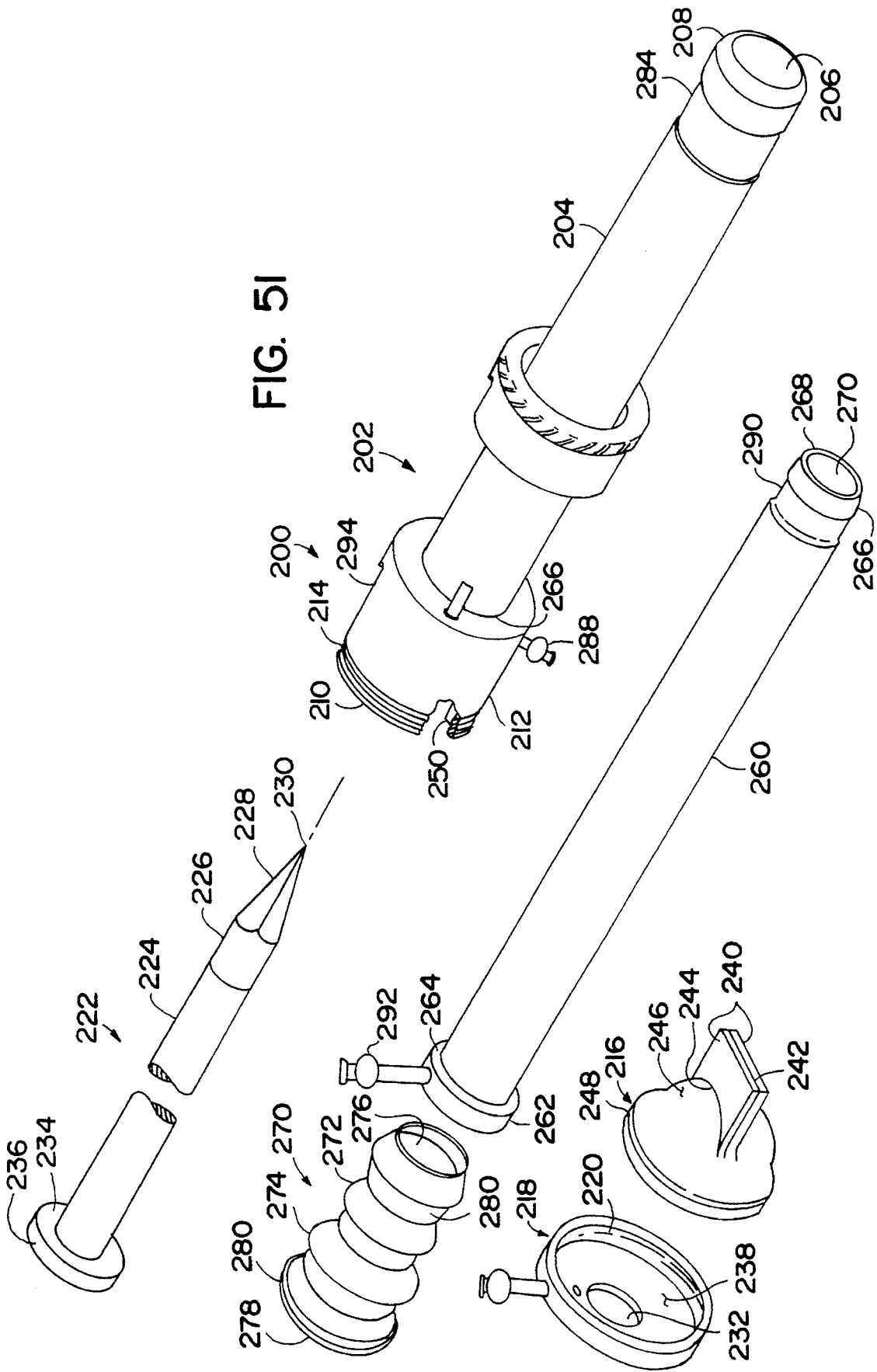
FIG. 51 is an exploded isometric view of a further embodiment of the invention.

A further alternative embodiment of the subject invention is depicted in FIG. 51, which illustrates an assembly of a surgical instrument, generally designated by reference numeral 200, dedicated to puncturing an anatomical organ structure such as a cavity wall, and providing a passageway via the puncture wound for communicating with the interior of the cavity. The instrument 200 has an outer cylindrical sleeve 202 having an elongated section 204 with an interior lumen 206 opening into a distal end 208 and extending through to its proximal end 210. Sleeve 202 may have an enlarged cross-section 212 at its proximal end terminating in a male threaded coupling 214. A valve assembly, such as a nipple valve 216 made of a flexible elastic material is insertable into the open proximal end of enlarged cross-section 212, to serve as a flexible seal and thereby prevent egress or escape of fluids to or from an anatomical organ cavity via sleeve 202. The nipple valve 216 is preferably of the type that is disclosed in my U.S. Pat. No. 4,535,773, the disclosure of which is incorporated by reference herein. A cap 218 bearing female threads 220 corresponding to those of coupling 214 is provided to engage the proximal end of section 212.

A trocar 222, having an elongated shaft 224 terminating at its distal end 226 in a multi-sided blade 228 of surgical steel forming a sharp point 230, may be introduced into the proximal end of valve assembly 216, via a central aperture 232 in cap 218. The diameter of opening 232 is approximately equal in diameter to the diameter of the trocar shaft 224, thereby enabling the trocar blade 228 and shaft 224 to be pushed longitudinally through cap 218, through valve assembly 216, and to pass through the length of sleeve 202. After shaft 224 has been pushed through and engaged by the sides of the nipple valve 216, and fully inserted into the sleeve lumen 206, the forward rim 234 of a knob 236 extending from the proximal end of the trocar 222 will abut against the base surface 238 of cap 218, while the trocar blade 228 and point 230 thereof will protrude beyond the distal end 208 of interior lumen 206.

Nipple valve 216 is inserted into the proximal end of cross-section 212 to provide a substantially air-tight gate. The nipple valve 216 is comprised of a pair of generally planar flaps 242 forming either side of a single teat 242. The valve flaps 240 are attached along generally parallel-oriented arcs 244 to the bowl 246 of the convex side of valve. The bowl 246 terminates with a flange 248 which rests against an internal shoulder 250 formed inside the proximal end of sleeve section 212.

A hollow, thin-walled tubular inner sleeve 260 having a flange 262 connected by a (preferably sloped) shoulder 264 at its proximal end and a tapered distal end 266 of reduced cross-section, may be placed inside the outer sleeve 202 before the nipple valve 216 is inserted into the section 212 and the cap 218 advanced along threads 214. The tapered distal end 266 of the inner sleeve may form a thin, blunt bearing surface 268 which is preferably configured so as not to cut or otherwise traumatise anatomical tissue. A lumen 270 extends coaxially through the axial length and opens at opposite ends of inner sleeve 260 to receive and allow axial reciprocation of the trocar shaft 224. When pushed toward the distal end 208 of the outer sleeve 202, the flange 262 will seat against the junction 266 between the lesser and greater cross-sections of the sleeve 202. The reduced cross-section of the inner sleeve distal end 260 preferably forms a close fit against the circumferential surface of the distal end 226 of the trocar 222 to enhance control of the trocar within the sleeve.

A compression spring 270 coiled into a distal section 272 of lesser cross-sectional diameter and a proximal section 274 of greater cross-sectional diameter, and completely covered except at opposite base orifices 276, 278 by an air-tight web 280 of a flexible, elastic material, may be inserted into outer sleeve section 212 with the rim of base orifice 276 seated against flange 262 and with the spring rim 280 seated between the internal shoulder 250 inside the proximal end of the outer sleeve section 212 and the flange 248 on the convex side of the nipple valve 216 while receiving the closed planar valve flaps 240. Closed compression spring 270 forms an air-tight seal between flange 262 and the inside base surface 238 of the cap 218.

With reference to FIGS. 51 and 52, the wall structure of elongated section 204 may be optionally made hollow, and the distal end portion of the outer wall thereof can be divided by a circumferential gap. An expansible thin-wall membrane 284 which can be in the form of a flexible, elastic material such as the balloon material described above extends circumferentially around the elongated section 204 and axially across the gap to connect axially separated portions of the distal portion of the sleeve section. A stop cock 288 fitted to the outer sleeve proximal section 212 enables a fluid, such as a liquid or gaseous phase substance, to be introduced between the inner and outer walls of section 204. When placed under pressure, the fluid will cause the balloon 284 to expand radially outward, circumferentially around the distal portion of the outer sleeve section 204, to form the radially extending balloon shown in FIG. 52.

Alternatively, or in combination with the outer sleeve structure described immediately above, the wall structure of the elongated inner sleeve 260 may be made hollow, and the distal end portion of the outer wall thereof may be divided by a circumferential gap, and an expansible thin-wall membrane 290 made of a flexible, elastic material extends circumferentially around sleeve 260 and axially across the gap to connect axially separated portions of the distal portion of the sleeve 260. A stop cock 292 enables a liquid or gaseous phase fluid to be introduced between the inner and outer walls of the sleeve 260. A slot 294 formed in the outer sleeve proximal section 212 accommodates the stop cock 292 upon insertion of the inner sleeve 260. When placed under pressure, the fluid will cause membrane 290 to expand radially outward, circumferentially around the distal portion of sleeve 260, to form the second radially extending balloon shown in FIG. 52.

After the inner sleeve 260 has been axially positioned inside the outer sleeve 202, and spring 270 and valve 216 have been inserted within the sleeve section 212 and seated between flange 262 and shoulder 250, cap 218 is rotated against outer sleeve proximal end 210 to enable threaded sections 214 and 220 to threadingly engage. The length of the trocar shaft 224 should be sufficient to enable at least the trocar blade 228 and point 230 thereof to extend completely through the outer sleeve lumen 206 and beyond distal end 208 when the shaft 224 has been fully inserted through the cap orifice 232, between valve flaps 240, coaxially through spring 270 and into lumen 206, with trocar shoulder 234 seated against the exterior base surface of the cap. The compression load applied by the spring 270 on the inner sleeve flange 262, however, will force the distal end 266 of the inner sleeve to protrude from the lumen 206 and beyond the distal end of the outer sleeve, to the otherwise exposed distal blade 228 and point 230 of the trocar 222. The length of the inner sleeve 260 should be sufficient when shoulder 264 is seated against the interior surface of junction 266, to not only completely shield the trocar blade 228 and point thereof when the trocar 222 is fully inserted into lumina 206 and 270, but to completely expose membrane 290. Force applied to the inner sleeve distal end 268 against the force of spring 270 permits the inner sleeve 260 to axially reciprocate within the outer sleeve 204 in accordance with the relative loading of the force applied and the bias of the spring 270.

As shown in FIG. 52, either or both the outer sleeve 204 and inner sleeve 260 may be constructed with one or more radially expansible balloons 284, 290. If the instrument 200 is constructed with only one of the two depicted balloons, that balloon will, upon inflation, adjoin the interior wall adjacent to layer e of the anatomical organ structure after insertion of the distal end of instrument and inflation of the balloon. In its inflated position adjacent the interior cavity wall of the anatomical organ structure, the balloon not only anchors its sleeve of the instrument 200 in place, but provides an expanded member enabling a surgeon to gently draw the anatomical cavity wall away from other anatomical organ structures included within the cavity, thereby lessening or completely dispensing with the need for gaseous insufflation. The presence of a second balloon on the instrument additionally endows the surgeon with an ability to use the second balloon, such as balloon 290, disposed axially outwardly from the first balloon 284 positioned immediately adjacent the interior cavity wall, to manipulate the anatomical organ structures within the cavity without the necessity of introducing another instrument through lumina 206 and 270.

The methods and instruments disclosed may be used to provide communication through the walls of various anatomical cavities in human and animal patients. By selecting a suitable length and diameter for the instrument and the implement which it accommodates (e.g., trocar or cannula), the instrument may be made suitable for puncturing the walls of such cavities as a blood vessel, a spinal cavity, a subarachnoid space, an ear ventricle, an abdominal cavity, or a joint cavity. After piercing a cavity wall, a needle implement, for example, may be left in place and used to inject or withdraw gaseous or liquid phase fluids from the cavity.

It is apparent from the foregoing description that the surgical methods and puncturing instruments disclosed herein both facilitate endoscopic surgery while minimizing risk of various patient mortality and morbidity. Once the distal portion of the elongate structure has been inserted into an organ cavity, introduction of a fluid under pressure through the port and into the chamber causes the membrane to inflate circumferentially around the distal portion and uniformly extend radially outwardly from the elongate member on the interior side of the anatomical cavity wall, thereby anchoring the distal portion of the elongate member within the cavity wall incision while enabling a surgeon to grasp and use the elongate member to gently draw the cavity wall away from the organ structure internal to the cavity without direct gaseous phase insufflation of the anatomical cavity. To further enhance patient safety, these methods and instruments may be used in conjunction with several of the safety puncturing instruments and methods disclosed in my earlier mentioned U.S. Pat. No. 4,535,773, as for example, where a reciprocating, bias loaded, shielding sleeve is interposed between the blade of a trocar and the hollow-walled outer elongate member of a trocar. Alternatively, a reciprocating shielding sleeve itself may be constructed as a hollow-walled, air-tight chamber with a distal portion containing a thin-wall expansible membrane, as disclosed herein. Moreover, both the outer elongate member and the reciprocating shielding sleeve may be individually constructed as hollow-walled, air-tight chambers with distal portions containing circumferential thin-wall expansible membranes, as disclosed herein.

What is claimed is:

1. A medical instrument for manipulating internal organs of a body, comprising;

a rod, having a retractor body arranged at a distal end of the rod and a handle at a proximal end of the rod;

a rigid flexion resisting shaft, having a proximal end and a distal end, for guiding said rod, said rod being movable with respect to the shaft in an axial direction of said rod;

wherein said retractor body comprises a multi-joint lever system of articulated arms connected to one another to be pivotably movable, which can be brought into an open position by movement of the rod in a first direction with respect to the shaft, and can be brought into a closed position by movement of the rod in a second direction with respect to the shaft;

wherein said multi-joint lever system comprises two pairs of articulated arms, each pair having a proximal end, a distal end and a central joint where two articulated arms are joined by a hinge, each pair being assigned to an opposite side of said rod guided by said shaft, said distal end of each pair being pivotally connected to said distal end of said rod and said proximal end of each pair being pivotally connected to said distal end of said shaft.

* * * * *